United States Patent [19]
Ryan et al.

[11] Patent Number: 5,296,449
[45] Date of Patent: Mar. 22, 1994

[54] SYNERGISTIC COMPOSITION AND METHOD OF SELECTIVE WEED CONTROL

[75] Inventors: Patrick Ryan, Bar Hill, England; Urs Hofer, Rheinfelden, Switzerland; Richard Istead, Bottmingen, Switzerland; Hans Gut, Wallbach, Switzerland; Wolfgang P. Iwanzik, Sisseln, Switzerland

[73] Assignee: Ciba-Geigy Corporation, Ardsley, N.Y.

[21] Appl. No.: 975,250

[22] Filed: Nov. 12, 1992

[30] Foreign Application Priority Data

Nov. 15, 1991 [CH] Switzerland ............... 3326/91
Jun. 9, 1992 [CH] Switzerland ............... 1835/92

[51] Int. Cl.$^5$ ............... A01N 43/76; A01N 43/40; A01N 35/06; A01N 25/32
[52] U.S. Cl. ............... 504/105; 504/130; 504/138; 504/148
[58] Field of Search ............... 71/94, 121; 504/130, 504/138, 148, 105

[56] References Cited

U.S. PATENT DOCUMENTS

| | | | |
|---|---|---|---|
| 4,505,743 | 3/1985 | Schurter et al. | 71/94 |
| 4,666,510 | 5/1987 | Watson et al. | 71/103 |
| 4,713,109 | 12/1987 | Schurter et al. | 71/94 |
| 4,874,421 | 10/1989 | Kleschick | 71/9 |
| 4,881,966 | 11/1989 | Nyffeler et al. | 71/94 |
| 5,050,269 | 9/1991 | Barton et al. | 71/88 |

FOREIGN PATENT DOCUMENTS

| | | |
|---|---|---|
| 587549 | 12/1987 | Australia . |
| 627582 | 12/1990 | Australia . |
| 1236106 | 5/1988 | Canada . |
| 0080301 | 6/1983 | European Pat. Off. . |
| 0128642 | 12/1984 | European Pat. Off. . |
| 0248968 | 12/1987 | European Pat. Off. . |
| 0400585 | 12/1990 | European Pat. Off. . |

OTHER PUBLICATIONS

The Pesticide Manual, Ninth Edition, Editor Charles R. Worthing, p. 365 (1989).

Synergistic Mixtures, Harker & O'Sullivan pp. 310–316 (1991).
Brighton Crop Protection (1989) pp. 729–734 D. W. Cornes.

*Primary Examiner*—Richard L. Raymond
*Assistant Examiner*—B. Bembenick
*Attorney, Agent, or Firm*—Kevin T. Mansfield; Edward McC. Roberts

[57] ABSTRACT

Herbicidal composition comprising 5-(2,4,6-trimethylphenyl)-2-[1-(ethoximino)propionyl]-cyclohexane-1,3-dione of formula I

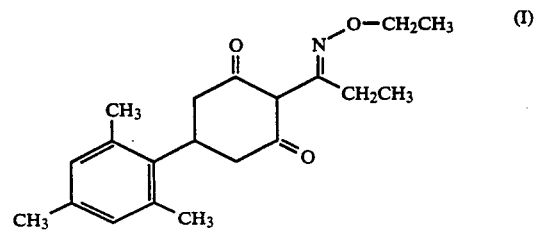

and a synergistically effective amount of either 2-[4-(5-chloro-3-fluoropyridin-2-yloxy)phenoxy]-propionic acid propynyl ester of formula II

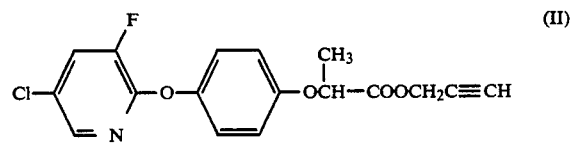

or (±)-2-[4-(6-chlorobenzoxazol-2-yloxy)phenoxy]propionic acid ethyl ester of formula III

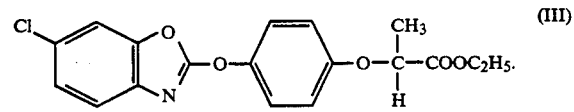

13 Claims, No Drawings

SYNERGISTIC COMPOSITION AND METHOD OF SELECTIVE WEED CONTROL

The present invention relates to a synergistic composition, comprising a herbicidal active ingredient combination, that is outstandingly suitable for selective weed control in crops of useful plants, especially in crops of cereals, soybeans, cotton rice and vegetables and in lawns.

The invention relates also to a method of controlling weeds in crops of useful plants, preferably in crops of cereals, soybeans, cotton, rice and vegetables and in lawns, and to the use of the novel composition.

The compound 5-(2,4,6-trimethylphenyl)-2-[1-(ethoximino)-propionyl]-cyclohexane-1,3-dione (tralkoxydim) is known as a selective herbicide. That active ingredient, its preparation and its use are described in European Patent Applications Nos. 0 128 642 and 0 080 301.

Other known selective herbicides for use against weeds in crops of useful plants are 2-[4-(5-chloro-3-fluoropyridin-2-yloxy)-phenoxy]-propionic acid propynl ester and ($\pm$)-2-[4-(6-chlorobenzoxazol-2-yloxy)-phenoxy]propionic acid ethyl ester (fenoxapropethyl). 2-[4-(5-Chloro-3-fluoropyridin-2-yloxy)-phenoxy]-propionic acid propynyl ester, its preparation and its use are described in U.S. Pat. No. 4,713,109 (R-enantiomer) and U.S. Pat. No. 4,505,743 (racemate). Fenoxapropethyl is known from the Pesticide Manual, 8th Edition, page 379, British Crop Protection Council, The Lavenham Press Limited, Suffolk.

Surprisingly, it has now been found that a quantitatively variable combination of the active ingredients has a synergistic effect that is capable of controlling the majority of the weeds occurring in crops of useful plants, both using the preemergence method and using the postemergence method, without damaging the useful plants.

There is therefore proposed in accordance with the present invention a novel synergistic composition for selective weed control that comprises as active ingredient 5-(2,4,6-trimethylphenyl)- 2-[1-(ethoximino)-propionyl]-cyclohexane-1,3-dione of formula I

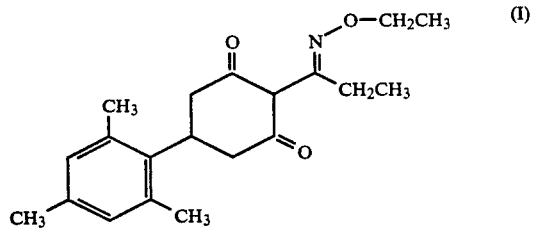

and a synergistically effective amount of either 2-[4-(5-chloro-3-fluoropyridin-2-yloxy)phenoxy]-propionic acid propynyl ester of formula II

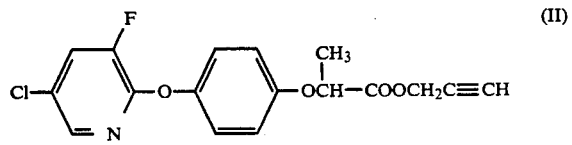

or ($\pm$)-2-[4-(6-chlorobenzoxazol-2-yloxy)phenoxy]propionic acid ethyl ester of formula III

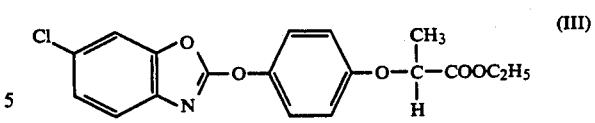

in admixture with one another.

It is extremely surprising that the combination of the compound of formula I with the compound of formula II or III not only brings about the additive increase in the activity spectrum against the weeds to be controlled that is to be expected in principle, but achieves a synergistic effect that broadens the range of activity of the two compositions in two respects:

Firstly, the rates of application of the individual compounds of formulae I, II and III are reduced, while the quality of action remains the same. Secondly, the combined mixture achieves a high degree of weed control even where the two individual compounds have become totally ineffective at very low rates of application. That results in a considerable broadening of the spectrum of weeds and an additional increase in the safety margin for the crops of useful plants, which is necessary and desirable in case of inadvertent active ingredient overdosing.

The active ingredient combination according to the invention comprises a compound of formula I and a compound of formula II or III in any desired mixing ratio, generally with an excess of one component over the other. Preferred mixing ratios of the compound of formula I and the co-component of formula II or III are from 100:1 to 1:1, especially from 50:1 to 2:1.

A combination of the R-enantiomer of the compound of formula II

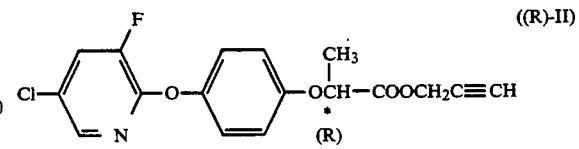

with the compound of formula I has proved to be an especially effective synergistic active ingredient mixture. The compound of formula II, especially of formula (R)-II, is preferably used together with an antidote. 1-Methylhexyl-2-(5-chloroquinolin-8-yloxy)acetate of formula A

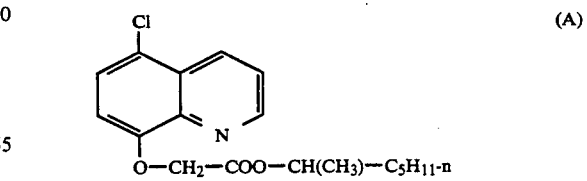

has proved to be an especially suitable antidote. That compound and its use are described, for example, in EP-A-0 191 736. The purpose of the antidote is to protect the cultivated plant against the phytotoxic action of the compound of formula II. The antidote of formula A has no herbicidal activity itself and is not capable of intensifying the herbicidal action of the compound of formula II.

In the case of a field treatment, which is carried out either using a tank mixture comprising a combination of an antidote of formula A and a herbicide of formula II or by applying an antidote of formula A and a herbicide of formula II separately, the ratio of antidote to herbicide is generally from 1:100 to 10:1, preferably from 1:20 to 1:1, and especially 1:1. In a very especially preferred combination of a herbicide of formula (R)-II and an antidote of formula A, the ratio of antidote to herbicide is 1:4.

The (±)-2-[4-(6-chlorobenzoxazol-2-yloxy)phenoxy]propionic acid ethyl ester of formula III

especially its (R)-enantiomer of formula (R)-III

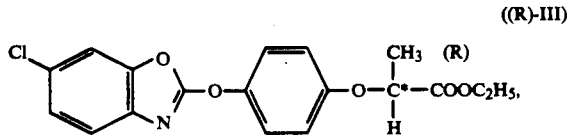

is used in the synergistic mixtures according to the invention preferably together with an antidote. Especially preferred is the compound of formula III with the antidote 1-(2,4-dichlorophenyl)-5-(trichloromethyl)-1H-1,2,4-triazole-3-carboxylic acid ethyl ester (fenchlorazol-ethyl) of formula B

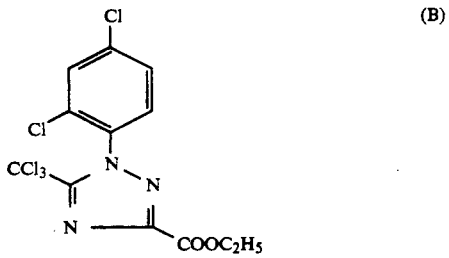

known from the Pesticide Manual, 9th Edition, page 365, British Crop Protection Council, The Lavenham Press Limited, Suffolk. The mixing ratio of antidote of formula B to herbicide of formula III is generally from 1:100 to 10:1, preferably from 1:20 to 1:1, and especially from 1:4 to 1:2. Very special preference is given to the use in the synergistic mixtures according to the invention of the antidote of formula B with the herbicide of formula (R)-III in a ratio of 1:2. The purpose of the antidote is to protect the cultivated plant from the phytotoxic action of the compound of formula III or (R)-III. The antidote of formula B has no herbicidal activity itself and is not capable of intensifying the herbicidal action of the compound of formula III or (R)-III.

The herbicidal active ingredient combinations according to the invention are outstandingly suitable for selective weed control in crops of useful plants, especially in crops of cereals, soybeans, cotton, rice and vegetables. Especially outstanding activity against weeds has been observed in cereal crops.

The herbicidal active ingredient combinations according to the invention can be used to control a large number of agronomically important weeds, such as Avena fatua, Alopecurus myosuroides and Apera spica venti, both using the preemergence method and using the postemergence method, but preferably the postemergence method. The active ingredient combination according to the invention controls especially monocotyledonous weeds.

The rate of application can vary within a wide range and depends on the nature of the soil, the type of application (pre- or post-emergence; seed dressing; application to the seed furrow; no tillage application, etc.), on the cultivated plant, the weed to be controlled, the prevailing climatic conditions and on other factors determined by the type of application, the time of application and the target crop. In general, the active ingredient mixture according to the invention can be used at a rate of application of from 1 to 0.01 [kg of active ingredient/ha], especially from 0.5 to 0.05 [kg of active ingredient/ha].

The mixtures of a compound of formula I with a compound of formula II or III are used in unmodified form, as obtainable from synthesis, or, preferably, together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compounds (active ingredients) of formulae I and II or III and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, also silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"Mc Cutcheon's Detergents and Emulsifiers Annual". Mc Publishing Corp., Glen Rock, N.J., 1988.

M. and J. Ash, "Encyclopedia of Surfactants", Vol. I-III, Chemical Publishing Co., New York, 1980–1981.

Dr. Helmut Stache "Tensid-Taschenbuch", Carl Hanser Verlag, Munich/Vienna 1981.

The herbicidal compositions generally comprise 0.1 to 99%, preferably 0.1 to 95%, of a mixture of a compound of formula I with a compound of formula II or III, 1 to 99% of a solid or liquid adjuvant and 0 to 25%, preferably 0.1 to 25%, of a surfactant.

Whereas commercial products will preferably be formulated as concentrates, the end user will normally employ dilute formulations.

The compositions may also comprise further additives such as stabilisers, for example vegetable oils and epoxidised vegetable oils (epoxidised coconut oil, rape oil or soybean oil), antifoams, for example silicone oil, preservatives, viscosity regulators, binders and tackifiers, as well as fertilisers or other active ingredients for obtaining special effects.

Preferred formulations have especially the following composition (throughout, percentages are by weight):

Emulsifiable Concentrates active ingredient
mixture: 1 to 90%, preferably 5 to 20%
surface active agent: 1 to 30%, preferably 10 to 20%
liquid carrier: 5 to 94%, preferably 70 to 85%

Dusts active ingredient
mixture: 0.1 to 10%, preferably 0.1 to 1%
solid carrier: 99.9 to 90%, preferably 99.9 to 99%

Suspension Concentrates active ingredient
mixture: 5 to 75%, preferably 10 to 50%
water: 94 to 24%, preferably 88 to 30%
surface active agent: 1 to 40%, preferably 2 to 30%

Wettable Powders active ingredient
mixture: 0.5 to 90%, preferably 1 to 80%
surface active agent: 0.5 to 20%, preferably 1 to 15%
solid carrier: 5 to 95%, preferably 15 to 90%

Granules active ingredient
mixture: 0.5 to 30%, preferably 3 to 15%
solid carrier: 99.5 to 70%, preferably 97 to 85%

BIOLOGICAL EXAMPLES

A synergistic effect exists whenever the action of the active ingredient combination I and II or III is greater than the sum of the action of the active ingredients applied individually.

The herbicidal action to be expected Ae for a given combination of two herbicides can be calculated (see COLBY, S. R., "Calculating synergistic and antagonistic response of herbicide combinations", Weeds 15, pages 20–22, (1967)) as follows:

$$Ae = X + \frac{Y \cdot (100 - X)}{100}$$

in which:
- X = percentage growth inhibition in the case of treatment with a compound of formula I at a rate of application of p kg per hectare in comparison with the untreated control (=0%).
- Y = percentage herbicidal action in the case of treatment with a compound of formula II or III at a rate of application of q kg per hectare in comparison with the untreated control.
- Ae = expected herbicidal action (percentage growth inhibition in comparison with the untreated control) after treatment with the compounds of formulae I and II or III at a rate of application of p+q kg of active ingredient per hectare.

If the action actually observed is greater than the value to be expected Ae, synergism exists.

The synergistic effect of the combinations of a compound of formula I with a compound of formula II or III is demonstrated in the following Examples.

EXAMPLE B1

POSTEMERGENCE TEST

The seeds of the test plant are sown in a greenhouse in plastic pots containing 0.5 l of sterilised soil. The plants are sprayed post-emergence in the 2- to 3-leaf stage with an aqueous dispersion of the active ingredient combination. The desired rate of application of active ingredient is obtained by suitable dilution of the concentrate. 55 ml of dispersion are sprayed per $m^2$. The test plants are grown on in the greenhouse and are watered daily.

After 3 weeks the herbicidal action is evaluated in comparison with an untreated control group. The percentage inhibition of growth is recorded in comparison with the untreated control. The following linear scale is used:
- 100% = plants have died
- 50% = moderate action
- 0% = as untreated control The results of the comparison are recorded in Tables 1 to 5 together with the expected values calculated in accordance with the Colby formula. The formula numbers of the compounds used in each case and the rates of application as well as the tested weeds and cultivated plants are indicated.

TABLE 1

Synergistic action against *Avena fatua* postemergence:

| Compounds and rates of application in g AI/ha | expected value (in accordance with Colby) | measured inhibition of growth |
| --- | --- | --- |
| 10 g (R)-II* | — | 25 |
| 75 g I | — | 25 |
| 10 g (R)-II* + 75 g I | 44 | 90 |

*additionally comprises 2.5 g of the antidote 1-methylhexyl-2-(5-chloroquinolin-8-yl-oxy)acetate.

TABLE 2

Synergistic action against *Alopecurus myosuroides* postemergence:

| Compounds and rates of application in g AI/ha | expected value (in accordance with Colby) | measured inhibition of growth |
| --- | --- | --- |
| 10 g (R)-II* | — | 0 |
| 75 g I | — | 0 |
| 10 g (R)-II* + 75 g I | 0 | 99 |

*additionally comprises 2.5 g of the antidote 1-methylhexyl-2-(5-chloroquinolin-8-yl-oxy)acetate.

TABLE 3

Synergistic action against *Apera spica venti* postemergence:

| Compounds and rates of application in g AI/ha | expected value (in accordance with Colby) | measured inhibition of growth |
| --- | --- | --- |
| 10 g (R)-II* | — | 0 |
| 75 g I | — | 0 |
| 10 g (R)-II* + 75 g I | 0 | 90 |

*additionally comprises 2.5 g of the antidote 1-methylhexyl-2-(5-chloroquinolin-8-yl-oxy)acetate.

TABLE 4

Action of the compound mixture according to the invention against the cultivated plant winter barley postemergence:

| Compounds and rates of application in g AI/ha | expected value (in accordance with Colby) | measured inhibition of growth |
| --- | --- | --- |
| 10 g (R)-II* | — | 0 |
| 75 g I | — | 0 |
| 10 g (R)-II* + 75 g I | 0 | 0 |

*additionally comprises 2.5 g of the antidote 1-methylhexyl-2-(5-chloroquinolin-8-yl-oxy)acetate.

TABLE 5

Synergistic action against *Apera spica venti* postemergence:

| Compounds and rates of application in g AI/ha | expected value (in accordance with Colby) | measured inhibition of growth |
| --- | --- | --- |
| 20 g (R)-III* | — | 50 |
| 75 g I | — | 20 |
| 20 g (R)-III* + 75 g I | 60 | 95 |

*additionally comprises 10 g of the antidote 1-(2,4-dichlorophenyl)-5-(trichloromethyl)-1H-1,2,4-triazole-3-carboxylic acid ethyl ester.

F1. FORMULATION EXAMPLES

Mixtures of the compounds of formulae I and II and I and III (throughout, percentages are by weight)

| a) Wettable powders | a) | b) | c) | d) |
| --- | --- | --- | --- | --- |
| Mixture of a compound of formula I with a compound of formula II | 10% | 20% | 5% | 30% |
| sodium lignosulfonate | 5% | 5% | 5% | 5% |
| sodium laurylsulfate | 3% | — | 3% | — |
| sodium diisobutylnaphthalene-sulfonate | — | 6% | — | 6% |
| octylphenolpolyethylene glycol ether (7-8 mol of ethylene oxide) | — | 2% | — | 2% |
| highly dispersed silicic acid | 5% | 27% | 5% | 27% |
| kaolin | 67% | — | 67% | — |

The active ingredient mixture is thoroughly mixed with the adjuvants and the mixture is thoroughly ground in a suitable mill, affording wettable powders which can be diluted with water to give suspensions of the desired concentration.

| b) Emulsifiable concentrate | a) | b) | c) |
|---|---|---|---|
| Mixture of a compound of formula I with a compound of formula III | 5% | 5% | 12% |
| octylphenolpolyethylene glycol ether (4-5 mol of ethylene oxide) | 3% | 3% | 3% |
| calcium dodecylbenzenesulfonate | 3% | 3% | 2% |
| castor oil polyglycol ether (36 mol of ethylene oxide) | 4% | 4% | 4% |
| cyclohexanone | 30% | 30% | 31% |
| xylene mixture | 50% | 35% | 35% |

Emulsions of any required concentration can be obtained from such concentrates by dilution with water.

| c) Dusts | a) | b) | c) | d) |
|---|---|---|---|---|
| Mixture of a compound of formula I with a compound of formula II | 2% | 4% | 2% | 4% |
| talcum | 3% | 4% | 4% | 8% |
| kaolin | 95% | 92% | 94% | 88% |

Ready-for-use dusts are obtained by mixing the active ingredient mixture with the carrier and grinding the mixture in a suitable mill.

| d) Extruder granules | a) | b) | c) |
|---|---|---|---|
| Mixture of a compound of formula I with a compound of formula II | 5% | 3% | 5% |
| sodium lignosulfonate | 2% | 2% | 2% |
| carboxymethylcellulose | 1% | 1% | 1% |
| kaolin | 87% | 87% | 77% |

The active ingredient mixture is mixed and ground with the adjuvants, and the mixture is moistened with water. The mixture is extruded and then dried in a stream of air.

| e) Coated granules | a) | b) |
|---|---|---|
| Mixture of a compound of formula I with a compound of formula III | 1.5% | 3% |
| polyethylene glycol (mol. wt. 200) | 3% | 3% |
| kaolin | 94% | 9% |

The finely ground active ingredient mixture is uniformly applied, in a mixer, to the kaolin moistened with polyethylene glycol. Non-dusty coated granules are obtained in this manner.

| f) Suspension concentrate | a) | b) |
|---|---|---|
| Mixture of a compound of formula I with a compound of formula II | 20% | 20% |
| ethylene glycol | 10% | 10% |
| nonylphenolpolyethylene glycol ether (15 mol of ethylene oxide) | 6% | 6% |
| sodium lignosulfonate | 10% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 12% |

The finely ground active ingredient mixture is intimately mixed with the adjuvants, giving a suspension concentrate from which suspensions of any desired concentration can be obtained by dilution with water.

It is often more practical to formulate the compound of formula I and the co-component of formula II or III individually and then, shortly before they are used, to combine them in the desired mixing ratio in the applicator in the form of a tank mixture in water. In the Formulation Examples, the compound of formulae II and III can, if desired, be used with the antidote A and B, respectively, in the mixing ratios given above.

What is claimed is:

1. A herbicidal composition comprising 5-(2,4,6-trimethylphenyl)-2-[1-(ethoximino)propionyl]-cyclohexane-1,3-dione of formula I

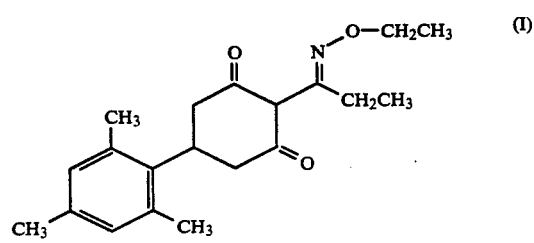

and a synergistically effective amount of either 2-[4-(5-chloro-3-fluoropyridin-2-yloxy)phenoxy]-propionic acid propynyl ester of formula II

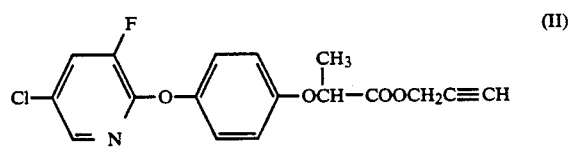

or (±)-2-[4-(6-chlorobenzoxazol-2-yloxy)phenoxy]propionic acid ethyl ester of formula III

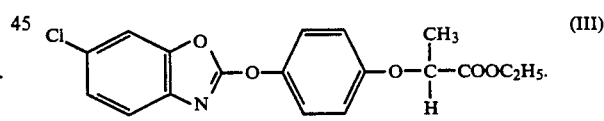

2. A composition according to claim 1 comprising 5-(2,4,6-trimethylphenyl)-2-[1-(ethoximino)-propionyl]-cyclohexane-1,3-dione of formula I

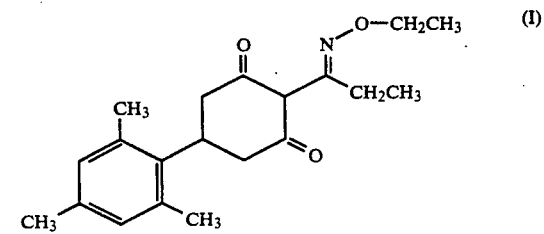

and a synergistically effective amount of 2-[4-(5-chloro-3-fluoropyridin-2-yloxy)phenoxy]-propionic acid propynyl ester of formula II

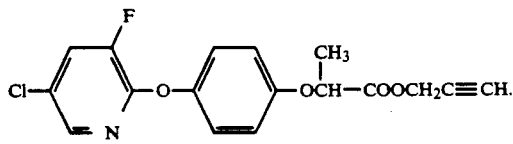

3. A composition according to claim 1 comprising 5-(2,4,6-trimethylphenyl)-2-[1-(ethoximino)-propionyl]-cyclohexane-1,3-dione of formula I

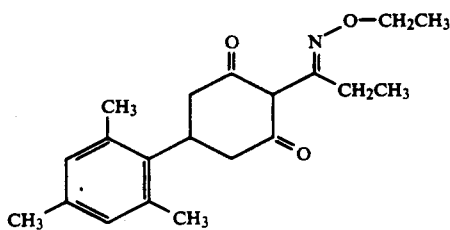

and a synergistically effective amount of (±)-2-[4-(6-chlorobenzoxazol-2-yloxy)phenoxy]-propionic acid ethyl ester of formula III

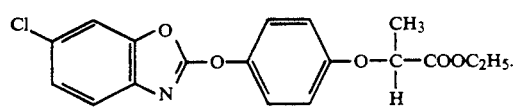

4. A composition according to claim 2 wherein the compound of formula II is in the form of the (R)-enantiomer.

5. A composition according to claim 3 wherein the compound of formula III is in the form of the (R)-enantiomer.

6. A composition according to claim 2 which additionally comprises 1-methylhexyl-2-(5-chloroquinolin-8-yloxy)acetate as antidote for the compound of formula II.

7. A composition according to claim 3 which additionally comprises 1-(2,4-dichlorophenyl)-5-(trichloromethyl)-1H-1,2,4-triazole-3-carboxylic acid ethyl ester as antidote for the compound of formula III.

8. A composition according to claim 1 wherein in the said composition the ratio by weight of the component of formula I to the component of formula II or III is from 100:1 to 1:1.

9. A method of controlling undesired plant growth in crops of useful plants, wherein a herbicidally effective amount of a composition according to claim 1 is applied to the cultivated plant area post-emergence.

10. A method according to claim 9 of controlling weeds in crops of cereals, soybeans, cotton, rice and vegetables and in lawns.

11. A method according to claim 10 of controlling weeds in cereals.

12. A method according to claim 9 of controlling monocotyledonous weeds.

13. A method according to claim 9 wherein the crops of useful plants are treated with the said composition at rates of application corresponding to a total amount of active ingredient of from 1 to 0.01 kg per hectane.

* * * * *